United States Patent [19]

Gough

[11] Patent Number: 4,810,698

[45] Date of Patent: Mar. 7, 1989

[54] S,S-DI(TERT-BUTYL) ETHYLPHOSPHONODITHIOATE AS PESTICIDES

[75] Inventor: Stanley T. D. Gough, White House Station, N.J.

[73] Assignee: May & Baker Ltd., Dagenham Essex, England

[21] Appl. No.: 828,270

[22] Filed: Feb. 11, 1986

Related U.S. Application Data

[63] Continuation of Ser. No. 703,602, Feb. 21, 1985, abandoned.

[51] Int. Cl.$^4$ .......................... A01N 57/02; C07F 9/40
[52] U.S. Cl. ..................................... 514/141; 558/214
[58] Field of Search .......................... 558/214; 514/141

[56] References Cited

U.S. PATENT DOCUMENTS

| | | | |
|---|---|---|---|
| 3,094,405 | 6/1963 | Toy et al. | 71/87 |
| 3,162,570 | 12/1964 | Wilson, Jr. | 514/141 |
| 4,472,390 | 9/1984 | Fahmy | 514/141 |

Primary Examiner—Anton H. Sutto
Attorney, Agent, or Firm—Burns, Doane, Swecker & Mathis

[57] ABSTRACT

S,S-Di(tert-butyl) ethylphosphonodithioate is disclosed as well as its use as an insecticide and nematocide, e.g. in controlling corn rootworm.

3 Claims, No Drawings

S,S-DI(TERT-BUTYL) ETHYLPHOSPHONODITHIOATE AS PESTICIDES

DESCRIPTION

This application is a continuation of my application Ser. No. 703,602 filed Feb. 21, 1985, now abandoned.

This invention relates to S,S-di(tert-butyl)ethylphosphonodithioate, pesticidal compositions which comprise it as active ingredient and to its use as an insecticide and nematocide.

The compound of the invention has the formula $CH_3CH_2—P(=O)[—SC(CH_3)_3]_2$ (formula I) and exhibits a wide range of insecticidal and nematocidal activity and possesses excellent stability and long residual activity particularly in soil.

The compound may be used, in particular, in agriculture, against adults, larvae and eggs of Lepidoptera (butterflies and moths), e.g. Heliothis spp. such as *Heliothis virescens* (tobacco budworm), *Heliothis armigera* and *Heliothis zea*, Spodoptera spp. such as *S. exempta*, *S. littoralis* (Egyptian cotton worm), *S. eridania* (southern armyworm), *Mamestra configurata* (bertha armyworm); Earias spp. e.g. *E. insulana* (Egyptian bollworm), Pectinophora spp. e.g. *Pectinophora gossypiella* (pink bollworm), Ostrinia spp. such as *O. nubilalis* (European cornborer), *Trichoplusia ni* (cabbage looper), Pieris spp. (cabbage worms), Laphygma spp. (armyworms), Agrotis and Amathes spp. (cutworms), Wiseana spp (porina moth), Chilo spp. (rice stem borer), Tryporyza spp. and Diatraea spp. (sugar cane borers and rice borers), *Sparganothis pilleriana* (grape berry moth), *Cydia pomonella* (codling moth), Archips spp. (fruit tree tortrix moths), *Plutella xylostella* (diamond back moth); against adults and larvae of Coleoptera (beetles) e.g. *Hypothenemus hampei* (coffee berry borer), Hylesinus spp. (bark beetles), *Anthonomus grandis* (cotton boll weevil), Acalymma spp. (cucumber beetles), Lema spp., Psylliodes spp., *Leptinotarsa decemlineata* (Colorado potato beetle), Diabrotica spp. (corn rootworms), Gonocephalum spp. (false wire worms), Agriotes spp. (wireworms), Dermolepida, Lepidiota and Heteronychus spp. (white grubs), *Phaedon cochleariae* (mustard beetle), *Lissorhoptrus oryzophilus* (rice water weevil), Meligethes spp. (pollen beetles), Ceutorhynchus spp., Rhynchophorus and Cosmopolites spp. (root weevils); Sitona spp. (pea and bean weevils); against Hemiptera e.g. Psylla spp., Bemisia spp., Aphis spp., Myzus spp., *Megoura viciae*, Phylloxera spp., Adelges spp., *Phorodon humuli* (hop damson aphid), Aeneolamia spp., Nephotettix spp. (rice leaf hoppers), Empoasca spp., Nilaparvata spp., Perkinsiella spp., Pyrilla spp., Aonidiella spp. (red scales), Coccus spp., Pseudococcus spp., Helopeltis spp. (mosquito bugs), Lygus spp., Dysdercus spp., Oxycarenus spp., Nezara spp., Hymenoptera e.g. Athalia spp. and Cephus spp. (saw flies), Atta spp. (leaf cutting ants); Diptera e.g. Hylemyia spp. (root flies), Atherigona spp. and Chlorops spp. (shoot flies), Phytomyza spp. (leaf miners), Ceratitis spp. (fruit flies); Thysanoptera such as *Thrips tabaci*; Orthoptera such as Locusta and Schistocerca spp. (locusts), crickets e.g. Gryllus spp. and Acheta spp and Gryllotalpidae (mole crickets); Collembola e.g. Sminthurus spp. and Onychiurus spp. (springtails), Isoptera e.g. Odontotermes spp. (termites), Dermaptera e.g. Forficula spp. (earwigs) and also other arthropods of agricultural significance such as Acari (mites) e.g. Tetranychus spp., Panonychus spp. and Bryobia spp. (spider mites), Eriophyes spp. (gall mites), Polyphagotarsonemus spp..; Blaniulus spp. (millipedes), Scutigerella spp. (symphilids), Oniscus spp. (woodlice) and Triops spp. (crustacea) and also plant-attacking nematodes infesting both roots and shoots such as cyst nematodes (Heterodera spp., Globodera spp.), root-knot nematodes (Meloidogyne spp.), lesion nematodes (Pratylenchus spp.), dagger nematodes (Xiphinema spp.) and stem and bulb eelworms (Ditylenchus spp.).

Since the activity of the compound against corn rootworm (Diabrotica sp.) is good and residual activity in soil is long, the compound of this invention is of special interest for controlling corn rootworm. The duration of residual activity in soil of the compound against corn rootworm is unexpectedly superior to that of compounds of related chemical structure, as has been demonstrated in the following experiment described in Example 1.

EXAMPLE 1

Experiment

The compounds tested were of the general formula:

| Compound | $R(X)P(=X^1)(X^2R^1)(X^3R^2)$ | | | | | (IA) | |
|---|---|---|---|---|---|---|---|
| | R | (X) | $X^1$ | $X^2$ | $R^1$ | $X^3$ | $R^2$ |
| A | Et | — | O | S | t-butyl | S | t-butyl |
| B | Et | — | O | S | n-propyl | S | t-butyl |
| C | Et | — | O | S | iso-propyl | S | t-butyl |
| D | Et | — | O | S | iso-butyl | S | t-butyl |
| E | Et | — | O | S | n-butyl | S | t-butyl |
| F | Me | — | O | S | n-propyl | S | t-butyl |
| G | Et | — | S | S | t-butyl | O | iso-propyl |
| H | Et | — | S | S | t-butyl | O | t-butyl |
| I | Et | O | O | S | t-butyl | S | t-butyl |
| J | Et | O | O | S | t-butyl | S | sec-butyl |

COMPOUND
A is the Compound of the present invention
B is Compound No. 2 of U.S. Pat. No. 4,472,390
C is Compound No. 7 of U.S. Pat. No. 4,472,390
D is Compound No. 9 of U.S. Pat. No. 4,472,390
E is Compound No. 10 of U.S. Pat. No. 4,472,390
F is Compound No. 12 of U.S. Pat. No. 4,472,390
G is Example 8 of U.S. Pat. No. 4,268,508
H is a congener of Compound A within U.S. Pat. No. 4,268,508
I is Compound No. 11 of PCT Patent Application No. WO 83/008870
J is Compound No. 10 of PCT Patent Application No. WO 83/008870

Test for Residual Activity and Persistence Against Corn Rootworm (Diabrotica sp.)

Test Method

The soil used was a clay-loam having a water content of approximately 23% of the oven-dry weight (determined by drying a sample for 24 hours at 110° C.). All rates of the treatments with the test compound were expressed as parts per million (ppm) of the oven-dry weight of the soil. Before treatment with the test compound, the soil was passed through a 3.5 mm aperture screen.

The test compound was dissolved in dimethyl ketone to give concentrations such that the addition of 1 ml quantities of the solution to soil samples equivalent to 100 g of oven-dry soil, gave concentrations of 0.1 and 0.5 ppm, and, in some cases, 0.05 ppm, of test compound.

Soil samples equivalent to 500 g of oven-dried soil were placed in polyethylene bags and 5 ml of solution of the test compound in dimethyl ketone containing the desired concentration of test compound was added. The contents of the bags were then thoroughly mixed. The bags were then opened for one hour to allow dimethyl ketone vapour to disperse.

Samples of soil taken from the bags were tested immediately for activity against *Diabrotica undecimpunctata* (Day 0). The remaining soil was then stored in sealed dark glass jars at 24° C. and further samples were taken and tested on the 7th, 14th, 21st, 28th, 42nd 56th, 70th and 84th day after treatment with the test compound (Days 7, 14, 21, 28, 42, 56, 70 and 84), the soil being remixed before withdrawal of the sample.

Activity against Diabrotica was determined by the following procedure:

Diabrotica were reared at 25° C. on maize seedlings.

Approximately 20 g of treated soil was placed in a 25×75 mm glass vial containing 2.5 ml of distilled water and a sprouted maize seedling with good root development, Five 5-day old Diabrotica larvae were placed upon the soil and any not burrowing into the soil after a few minutes were replaced until all the larvae had burrowed into the soil. The tube was covered with a wire mesh lid and kept at 25° C. for four days. Each treatment was replicated four-fold, up to and including Day 42, two replicates being used on Days 56, 70 and 84. After the four day period, the samples were examined, the numbers of dead and living larvae were counted and the mean percentage mortality of larvae calculated from the four replicate treatments in comparison with untreated controls.

A mean percentage mortality of 90 or greater indicates a satisfactory level of control of Diabrotica sp larvae.

The results obtained are shown in the following Tables I and II.

TABLE I

| Test Compound | Concentration of Test Compound (ppm) | Mean percentage mortality of Diabrotica larvae DAY | | | | | | | | |
|---|---|---|---|---|---|---|---|---|---|---|
| | | 0 | 7 | 14 | 21 | 28 | 42 | 56 | 70 | 84 |
| A | 0.5 | 100 | 100 | 100 | 100 | 100 | 100 | 100 | 100 | 100 |
|   | 0.1 | 100 | 100 | 100 | 90 | 95 | 90 | 30 | 20 | 0 |
|   | 0.05 | 90 | 95 | 100 | 35 | 40 | 16 | 10 | 0 | 0 |
| B | 0.5 | 100 | 100 | 100 | 95 | 100 | 0* | | | |
|   | 0.1 | 95 | 30 | 0 | 0* | | | | | |
| C | 0.5 | 100 | 100 | 100 | 100 | 100 | 100 | 50* | 70* | |
|   | 0.1 | 100 | 85 | 60 | 15 | 10 | 0* | | | |
|   | 0.05 | 30 | 25 | 0 | 0* | | | | | |
| D | 0.5 | 100 | 100 | 100 | 100 | 75 | 5 | 0* | | |
|   | 0.1 | 30 | 20 | 5 | 10 | 5 | 0* | | | |
| E | 0.5 | 100 | 70 | 30 | 5 | 0* | | | | |
|   | 0.1 | 0 | 10 | 0 | 0* | | | | | |
| F | 0.5 | 100 | 95 | 10 | 0* | | | | | |
|   | 0.1 | 35 | 5 | 0 | 0* | | | | | |
| G | 0.5 | 30 | 0* | | | | | | | |
|   | 0.1 | 5 | 0* | | | | | | | |
| H | 0.5 | 35 | 0* | | | | | | | |
|   | 0.1 | 0 | 0* | | | | | | | |
| I | 0.5 | 100 | 100 | 100 | 100 | 100 | 90 | 0* | | |
|   | 0.1 | 20 | 0 | 0 | 0* | | | | | |
| J | 0.5 | 100 | 90 | 80 | 50 | 75 | 16 | 10 | 0* | |
|   | 0.1 | 0 | 5 | 0 | 0* | | | | | |

*Testing terminated after this test.

TABLE II

| Test Compound | Persistence of mean percentage mortality of 90 or greater against Diabrotica larvae (Days) Concentration of Test Compound (ppm) | | |
|---|---|---|---|
| | 0.5 | 0.1 | 0.05 |
| A | gt 84 | 42–56 | 14–21 |
| B | 28–42 | 0–7 | — |
| C | 56–70 | 0–7 | + |
| D | 21–28 | + | — |
| E | 0–7 | + | — |
| F | 7–14 | + | — |
| G | + | + | — |
| H | + | + | — |
| I | 42–56 | + | — |
| J | 7–14 | + | — |

"gt" means "greater than"
"—" means "not tested"
"+" means that the mean percentage mortality did not reach 90 on Day 0
An indicated range, e.g. "42–56" means that the mean percentage mortality fell below 90 between these Days From the above results, it will be seen that:

(1) At a concentration of 0.1 ppm, Compound A gave a satisfactory level of control of Diabrotica larvae for more than six times as long as Compound B, Compound A having been shown to give a satisfactory level of control up to Day 42, whereas Compound B had ceased to give a satisfactory level of control by Day 7. Even at a concentration five times greater (0.5 ppm), Compound B ceased to give a satisfactory level lof control between Day 28 and Day 42.

Furthermore, Compound A gave a satisfactory level of control up to Day 14 even at the low concentration of 0.5 ppm, whereas, as mentioned above, Compound B had ceased to give satisfactory control by Day 7 even at a concentration twice as great (0.1 ppm).

(2) At a concentration of 0.1 ppm, Compound A gave a satisfactory level of control of Diabrotica larvae for more than six times as long as Compound C, Compound A having been shown to give a satisfactory level of control up to Day 42, whereas Compound C had ceased to achieve a mean percentage mortality of 90% by Day 7. At half this concentration (0.05 ppm), Compound A gave a satisfactory level of control up to Day 14, whereas Compound C did not achieve this level of activity even on Day 0.

(3) Even at a concentration of 0.5 ppm, Compound D ceased to give a satisfactory level of control of Diabrotica larvae by Day 28, whereas, in contrast, Compound A gave satisfactory control for twice as long, up to Day 42, at a concentration five times lower (0.1 ppm). At a concentration of 0.1 ppm, Compound D failed to give satisfactory control even on Day 0, whereas Compound A gave satisfactory control at this concentration up to Day 42 and even at a concentration five times lower (0.05 ppm) gave satisfactory control up to Day 14.

(4) At a concentration of 0.5 ppm, Compound E had ceased to give a satisfactory level of control of Diabrotica larvae by Day 7, whereas even at a concentration five times lower (0.1 ppm), Compound A gave satisfactory control for more than six times longer, up to Day 42. Even at a concentration ten times lower (0.05 ppm), Compound A gave control for twice as long, up to Day 14, than was achieved by Compound E at 0.5 ppm. At a concentration of 0.1 ppm, Compound E showed little or no activity even on Day 0, whereas at this concentration, Compound A gave a satisfactory level of control up to Day 42 and even at half this concentration (0.05 ppm) gave a satisfactory level of control up to Day 14.

(5) At a concentration of 0.5 ppm, Compound F had ceased to give a satisfactory level of control of Diabrotica larvae by Day 14, whereas at a concentration five times lower (0.1 ppm) Compound A gave satisfactory control for at least three times longer, up to Day 42 and even at a concentration ten times lower (0.05 ppm), Compound A gave satisfactory control lasting twice as long, up to Day 14. At a concentration of 0.1 ppm, Compound F did not achieve a satisfactory level of control even on Day 0, whereas at this concentration Compound A gave a satisfactory level of control up to Day 42 and even at half this concentration (0.05 ppm) gave a satisfactory level of control up to Day 14.

(6) Neither Compound G nor Compound H gave a satisfactory level of control of Diabrotica larvae even on Day 0 at concentrations of 0.5 ppm and 0.1 ppm, whereas Compound A gave satisfactory levels of control up to Day 42 and Day 14, repectively, at concentrations only one fifth (0.1 ppm) and one tenth (0.05 ppm) as great, respectively, as the highest concentration (0.5 ppm) of Compound G and Compound H tested.

(7) At a concentration of 0.1 ppm, Compound I failed to give a satisfactory level of control against Diabrotica larvae even on Day 0, whereas at this concentration, Compound A gave satisfactory control up to Day 42 and even at a concentration five times lower (0.05 ppm) Compound A gave satisfactory control up to Day 14. At a concentration of 0.5 ppm, Compound I had ceased to give a satisfactory level of control by Day 56, whereas at that concentration Compound A gave satisfactory control up to Day 84 and even at a concentration five times lower (0.1 ppm) gave satisfactory control for a period comparable to that obtained by Compound I at a concentration five times greater (0.5 ppm).

(8) Even at a concentration of 0.5 ppm, Compound J had ceased to give a satisfactory level of control of Diabrotica larvae by Day 14, whereas Compound A, at a concentration five times lower (0.1 ppm) gave satisfactory control for at least three times longer, to Day 42 and at a concentration ten times lower (0.05 ppm) Compound A gave a satisfactory level of control which lasted twice as long, up to Day 14. At a concentration of 0.1 ppm Compound J failed to give satisfactory control even on Day 0, whereas at that concentration, Compound A gave satisfactory control up to Day 42 and even at a concentration five times lower (0.05 ppm) gave satisfactory control up to Day 14.

(9) At a concentration of 0.1 ppm, Compound A gave a satisfactory level of control of Diabrotica larvae which persisted for more than six times as long, i.e. at least up to Day 42, as the most persistent of the comparison compounds at 0.1 ppm (Compound B and Compound C), which at this concentration had ceased to give a satisfactory level of control of Diabrotica by Day 7, while none of the other seven comparison compounds gave a satisfactory level of control of Diabrotica even on Day 0.

(10) In terms of mean percentage mortality of Diabrotica produced at Days 21, 28 and 42 at a concentration of 0.1 ppm, the results given in Table I show that at Day 21, Compound A was six times more active than Compound C and nine times more active than Compound D and that at Day 28, Compound A was nine and a half times more active than Compound C and nineteen times more active than Compound D, the remaining seven comparison compounds having ceased to show activity by these Days, while at Day 42, Compound A produced 90% mean percentage mortality of Diabrotica, whereas all nine comparison compounds had ceased to show activity by Day 42.

The results given in Tables I and II clearly demonstrate the unexpected and substantial advantage of Compound A over the nine comparison compounds in terms both of persistence of a satisfactory level of control of Diabrotica and in activity against Diabrotica at given times after application of the test compounds. This is particularly well shown by consideration of the results obtained at a concentration of 0.1 ppm of test compound, where a satisfactory level of control of Diabrotica was obtained wih Compound A at least to Day 42, whereas one comparison compound at this concentration (Compound C) had ceased to give satisfactory control at Day 14, one comparison compound (Compound B) had ceased to give satisfactory control at Day 7 and the remaining seven comparison compounds failed to achieve satisfactory control on Day 0. Even at a concentration five times as high (0.5 ppm) only two of the comparison compounds (Compound C and Compound I) gave satisfactory control for as long as, or slightly longer than that given by Compound A at the five-fold lower concentration of 0.1 ppm and even here Compound C and Compound I had ceased to give satisfactory control by Day 56, while Compound A gave satisfactory control beyond Day 84 at a concentration of 0.5 ppm.

The following Examples 2 to 7 further illustrate the valuable insecticidal and nematocidal properties of S,S-di(tert-butyl)ethylphosphonodithioate (Compound A).

EXAMPLE 2

The Control of Corn Root-Worm on Field Maize

Compound A formulated as a 10% granule was applied in a band at the time of seed drilling to the soil of a plot of field maize infested with corn root-worm. The maize plants were later uprooted and their roots assessed for damage caused by corn root-worm (Diabrotica spp.) using a conventional root rating scale in which 6.0 represents maximum pest attack and 1.0 the absence of visible damage. The rates of application indicated below are those of Compound A in kilogrammes per hectare (kg/ha). The following results were obtained:

| Rates of application (kg/ha) | Root ratings Replicate plots | | | | |
|---|---|---|---|---|---|
| | A | B | C | D | mean |
| Compound A | | | | | |
| 0.84 | 2.1 | 2.2 | 2.1 | 1.8 | 2.05 |
| 0.56 | 2.6 | 2.1 | 2.4 | 1.9 | 2.25 |
| 0.28 | 2.8 | 2.8 | 2.9 | 2.3 | 2.70 |
| untreated control | 5.9 | 5.9 | 4.9 | 3.6 | 5.08 |

The low root ratings obtained in the Compound A treatments in comparison with those of the untreated controls demonstrate the high effectiveness of this compound against corn root-worm.

EXAMPLE 3

The Control of Seed Corn Maggot on Field Maize

Compund A formulated as a 20% granule was applied as a band or as an in-furrow treatment to the soil of a plot of field maize infested with seed corn maggot at an application rate of 1.12 kg/ha of Compound A, both treatments being made at the time of seed drilling. The efficacy of the treatment against the seed corn maggot (Hylemyia platura) was later determined by counting the fly pupae along sample lengths of a row. The numbers found in the treated plots were recorded as a percentage of those found in the untreated controls. The following results were obtained:

| Compound A at 1.12 kg/ha | pupae found as a percentage of those in the control |
|---|---|
| as a band treatment | 15 |
| as an in-furrow treatment | 30 |

The reduction of pupae by 85% and 70% respectively demonstrates the high activity of Compound A against seed corn maggot.

EXAMPLE 4

The Control of Mole Crickets in Turf

Compound A formulated as a 20% granule was applied to turf infested with mole crickets (species of Gryllotalpidae) at application rates equivalent to 5.56 and 11.2 kg/ha of Compound A. The mounds of soil produced by the insects were recorded before and after treatment. The following results were obtained:

| number of mounds | Compound A (kg/ha) | | Untreated control |
|---|---|---|---|
| | 5.6 | 11.2 | |
| pre treatment | 13.8 | | 7.3 |
| post treatment | 2.8 | | 8.3 |
| pre treatment | | 10.3 | 15.0 |
| post treatment | | 1.5 | 17.0 |

The large reduction in numbers of mounds from the pre to the post treatment counts demonstrates the usefulness of Compound A in the control of mole-crickets.

EXAMPLE 5

The Control of Pea and Bean Weevil Larvae on Field Beans

Compound A formulated as a 10% granule was applied in two experiments to the soil around emerging spring sown field beans in a plot infested with pea and bean weevil at rates equivalent to 1 kg/ha and 2 kg/ha of Compound A. Plots were replicated four times in Experiment 1 and three times in Experiment 2. Approximately seven weeks later plants were uprooted and the numbers of weevil larvae on the roots counted. The results were expressed as the mean percentage reduction in larval numbers in comparison with untreated control plants. The following results were obtained

| Compound A (kg/ha) | % reduction of larval numbers | |
|---|---|---|
| | Experiment 1 | Experiment 2 |
| 2 | 90.2 | 92 |
| 1 | 53.3 | 93.75 |

The large reduction in larval populations obtained with Compound A, particularly at the 2 kg/ha application rate in Experiment 1 and Experiment 2 and at the 1 kg/ha application rate in Experiment 2, demonstrates the effectiveness of this compound against pea and bean weevil larvae.

EXAMPLE 6

Test to Measure Effectiveness Against Cane White Grub

Compound A was dissolved in acetone and this solution was used to treat quantities of soil to give a range of known concentrations of the compound in the soil. After evaporating the solvent, the treated soil was placed in glass jars (about 110 g of soil per jar). Twenty jars were prepared for each concentration. Each jar then received one third-instar larvae of the cane white grub Lepidiota frenchi. Twenty-eight days later the mortalities of the larvae were assessed. The following results were obtained:

| Application rate of Compound A in mg/kg of soil | % mortalities corrected for those in the controls |
|---|---|
| 0.5 | 47 |
| 1.0 | 89 |
| 2.0 | 95 |
| 4.0 | 100 |
| 8.0 | 100 |

The results obtained demonstrate the high insecticidal activity of Compound A against cane white grubs.

EXAMPLE 7

Tests for Nematocidal Activity (a) *Ditylenchus dipsaci* (stem and bulb eelworm)

The nematodes were cultured on lucerne plants (cv. du Puits) in a glasshouse. Two or three months after initial infection, plants were harvested, washed and eggs and larvae of the nematodes recovered from them by steeping lacerated stems and leaves in water. After sieving, an inoculum suspension containing about 150 larvae per milliliter was prepared in distilled water.

Equal parts of uncontaminated soil, sieved to a particle size of 1 to 2 mm, and of river sand were mixed. To batches of this soil were added Compound A under test, previously dispersed in distilled water with the aid of Tween 80, to give the required range of dilutions of chemical in soil.

Plastic plant pots of 200 ml capacity were part filled with coarse untreated sand on which were sown 100 lucerne seeds per pot. The pots were then filled with chemically treated soil, except in the case of untreated controls where untreated prepared soil was used. Each pot was watered from above with 5 ml of the nematode suspension such that each pot received about 750 larvae. Pots were held at a moisture content optimum for seed germination and plant growth.

Twelve to fourteen days later, the lucerne seedlings were harvested and inspected for nematode attack. The efficiency of each treatment was determined as the percentage reduction in attack in comparison with the untreated controls. The following results were obtained in two experiments:

| Application rate of Compound A | % age reduction in attack compared with controls | |
|---|---|---|
| (kg/ha) | Experiment 1 | Experiment 2 |
| 100 | 100 | — |
| 50 | 100 | 100 |
| 25 | 80 | 100 |
| 10 | 50 | 70 |
| 5 | 50 | 80 |
| 1 | — | 60 |

("—" means "not tested at this application rate in this experiment")

(b) *Meloidogyne incognita* (Root-knot nematode)

The culture was maintained on tomato plants in a glasshouse. A standard root-knot nematode inoculum suspension of about 1500 eggs per milliliter of distilled water was prepared from washed, macerated and sieved roots. At least 10 to 15% of the eggs were at the embryonic larval stage.

Soil prepared for the experiments consisted of a mixture of equal parts of river sand, peat and uncontaminated soil prepared by hand-mixing. This was inoculated with enough egg suspension to give about 30,000 eggs per liter of soil. Compound A was dissolved in acetone and adsorbed onto a small quantity of Attaclay, the acetone then being removed by evaporation. Except for the untreated control soil, batches of soil were then hand mixed with the treated Attaclay to provide the required range of dilutions of the test chemical in the final batches of soil.

Two replicate plant pots were filled from each soil batch. These were watered and maintained in a humid atmosphere for two weeks. Two small tomato plants (cv. Marmande) were then transplanted into each pot, these being maintained in a glasshouse for a further four weeks.

The plants were then harvested, washed and the root galls counted. The efficacy of each treatment was determined on the percentage reduction in galling in comparison with the untreated controls. The following results were obtained in two experiments:

| Application rate of Compound A | % age reduction in attack compared with controls | |
|---|---|---|
| (kg/ha) | Experiment 1 | Experiment 2 |
| 100 | 100 | — |
| 50 | 100 | 100 |
| 25 | 100 | 100 |
| 10 | 100 | 90 |
| 5 | 50 | 0 |
| 1 | — | 0 |

("—" means "not tested at this application rate in this experiment")

The above results demonstrate the high level of activity against *Ditylenclus dipsaci* and the very high level of activity against *Meloidogyne ingcognita* of Compound A.

The compound of the invention can be prepared by methods known per se. (By the term 'methods known per se' as used in the present specification is meant methods heretofore used or described in the chemical literature). Preferably, the compound of this invention is prepared from a starting material which is an ethyl phosphonic halide. The ethyl phosphonic halide is reacted with 2-methylpropane-2-thiol in the presence of a base to arrive at the compound of this invention.

According to a feature of the invention the compound of formula I is prepared by the process which comprises reacting an ethyl phosphonic halide of the general formula $CH_3CH_2-P(=O)(-X)-X^1$ (general formula II) wherein X represents a halogen atom, preferably chlorine, and $X^1$ represents a halogen atom, preferably chlorine, or a tert-butylthio group $[SC(CH_3)_3]$ with, when $X^1$ represents a halogen atom, generally two molar equivalents or, when $X^1$ represents a tert-butylthio group, generally one molar equivalent of 2-methyl-propane-2-thiol, in the presence of a base, or with the thiol alkali metal, e.g. sodium, salt.

The process proceeds in accordance with the following Reaction Schemes A and B:

Reaction Scheme A
($X^1$ represents a halogen atom)

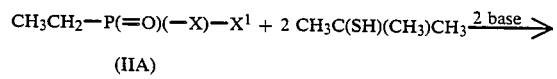

$CH_3CH_2-P(=O)(-X)-X^1 + 2\ CH_3C(SH)(CH_3)CH_3 \xrightarrow{2\ base}$ (IIA)

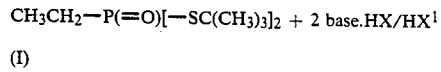

$CH_3CH_2-P(=O)[-SC(CH_3)_3]_2 + 2\ base.HX/HX^1$ (I)

Reaction Scheme B
$[X^1$ represents $-SC(CH_3)_3]$ $CH_3CH_2-P(=O)(-X)-SC(CH_3)_3\ +$ (IIB)

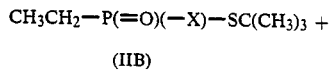

$CH_3C(SH)(CH_3)CH_3 \xrightarrow{base}$

-continued

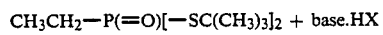

(I)

wherein X and $X^1$ are as hereinbefore defined. The reaction depicted in Reaction Scheme A is preferred for the preparation of the compound of the formula I.

The process is advantageously carried out at a temperature of about 0° C. to 100° C. in an organic solvent using an alkali metal salt of the thiol, prepared from the thiol and an alkali metal, e.g. sodium, or hydride thereof or an alkali metal hydroxide, e.g. sodium hydroxide.

Suitable organic solvents are, for example, benzene, toluene, cyclohexane, tetrahydrofuran, dimethylformamide, 2-butanone and acetone (dimethyl ketone).

Compounds of general formula II may be prepared by methods known per se. For example, the compounds of general formula IIA may be prepared by the procedures described by Morita et al, Tetrahedron Letters, 28, 2522–6 (1978), Morita et al, Chemistry Letters (1980), 435–8, British Pat. No. 1,374,757 and Pianfetti and Quin, J. Amer. Chem. Soc., 84, 851 (1962) and the compounds of general formula IIB may be prepared by the procedure described in published British patent application No. 2087891A. 2-Methyl-propane-2-thiol may be prepared by the procedure described by Dobbin, J. Chem. Soc., 57, 641.

The compound of this invention is effective as an insecticide and/or nematocide at low concentrations. Because of the small amounts of the compound required for effective control, it is generally impractical to apply the compound directly as such. Therefore, it is desirable that the compound be applied in the form of insecticidal or nematocidal compositions comprising S,S-di(tert-butyl)ethylphosphonodithioate in association with, and preferably homogeneously dispersed in, one or more compatible agriculturally-acceptable diluents or carriers and/or surface-active agents (i.e. diluents or carriers and/or surface active agents accepted in the art as being suitable for use in insecticidal or nematocidal compositions and which are compatible with the active ingredient).

Compositions for application comprising the active compound of this invention can be liquid dispersions or emulsions, preferably comprising from about 0.001% to about 1% w/v (weight/volume) of the active compound. Since the active compound is substantially water insoluble, it is desirable to add an inert, nonphytotoxic organic solvent to give a concentrate, which preferably comprises from about 2% to about 75% w/v of the active compound and which can be readily dispersed in an aqueous medium to produce a uniform dispersion of the active compound for application. The compositions will also usually comprise a surface-active agent. For example, an effective liquid composition can be prepared with the active compound, acetone or ethanol, water, and a surface-active agent such as Tween-20 (polyoxyethylene sorbitan monolaurate) or any of the other suitable surface-active agents.

The compositions containing the active compound can also be in solid, e.g. powdered or granular, form. For example, the active compound can be mixed with a suitable solid carrier such as kaolinite, bentonite, talc or the like, or incorporated into suitable granules, for example of mineral clays, e.g. attapulgite, montmorillonite, diatomite or sepiolite. Preferably, the compositions in powdered form comprise from about 0.5% to about 25% w/w (weight/weight) and the compositions in granular form preferably comprise from about 1% to about 25% w/w, of the active compound.

Compositions comprising the active compound may also comprise other pesticidal components, for example insecticides, nematocides and fungicides, e.g. thiofanox, carbofuran, aldicarb and benomyl.

For the control of insects and nematodes, the active compound is generally applied to the locus in which insect or nematode infestation is to be controlled at a rate of about 0.1 kg to about 25 kg of active compound per hectare of locus treated. Under ideal conditions, depending on the pest to be controlled, the lower rate may offer adequate protection. On the other hand, adverse weather conditions, resistance of the pest and other factors may require that the active ingredient be used in higher proportions.

When the pest is soil-borne, the formulation containing the active compound is distributed evenly over the area to be treated in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulation can, if desired, be distributed mechanically in the soil, for example by ploughing or disking. Application can be prior to planting, at planting, after planting but before sprouting has taken place or after sprouting.

The following Example illustrates the preparation of the compound of the present invention:

EXAMPLE 8

Preparation of S,S-di(tert-butyl)ethylphosphonodithioate

Sodium hydride (3.0 g, 0.125 mole) was suspended in dry tetrahydrofuran (70 ml) at 0° C. 2-methylpropane-2-thiol (14.1 ml, 0.125 mole) was then added dropwise over 15 minutes, keeping the temperature below 5° C. The mixture was then stirred at room temperature overnight, and ethylphosphonic dichloride (7.35 g, 0.05 mole) in dry tetrahydrofuran (10 ml) was then added over 30 minutes keeping the temperature below 35° C. by cooling with a water bath. The mixture was stirred at room temperature for 5 hours, and then let stand overnight.

Toluene (200 ml) was added, followed by water (200 ml), and the layers separated. The toluene layer was washed with 2N aqueous sodium hydroxide solution (100 ml), and water (100 ml) and then dried, filtered and evaporated to give S,S-di(tert-butyl)ethylphosphonodithioate in the form of an oil, (8.72 g) (69% yield).

The structure of the product was confirmed by its phosphorus NMR (nuclear magnetic resonance spectrum) (single peak at 65.0 ppm relative to 85% phosphoric acid), and by its proton NMR (tetramethylsilane as internal standard): singlet at 1.6 ppm [SC(CH$_3$)$_3$], two triplets at 1.1 ppm and 1.3 ppm (P-CH$_2$CH$_3$) and a multiplet at 2.2 ppm (P-CH$_2$CH$_3$). Integration of the proton magnetic spectrum was consistent with the depicted structure.

The following Example illustrates compositions according to the present invention:

EXAMPLE 9

A granular composition containing:

| | |
|---|---|
| S,S—di(tert-butyl) ethylphosphonodithioate | 10% w/w (weight/weight) |
| propylene glycol | 5% w/w |
| attapulgite 24/48 mesh granules | 85% w/w | was prepared by mixing the S,S-di(tert-butyl)ethylphosphonodithioate and propylene glycol and spraying the mixture through a flat-fan nozzle at a pressure of 2 bars onto the attapulgite granules, whilst mixing in a horizontal drum blender. After all the liquid had been sprayed onto the granules, mixing was continued for approximately 10 minutes until the liquid had been completely absorbed and the granules were homogenous. The granules thus obtained may be applied at a rate of 3 kg per hectare to a locus of infestation by Diabrotica spp. to control these species.

Granules containing 20% w/w of S,S-di(tert-butyl)ethylphosphonodithioate may be similarly prepared.

I claim:

1. A method for controlling corn rootworm which comprises providing a pesticidal amount in the soil of S,S-di(tert-butyl)ethylphosphonodithioate.

2. A composition for controlling insects and nematodes in soil comprising S,S-di(tert-butyl)ethylphosphonodithioate in an amount effective as an insecticide or a nematocide in soil and an inert non-phytotoxic organic solvent or a solid carrier.

3. S,S-Di(tert-butyl)ethylphosphonodithioate.

* * * * *